United States Patent [19]

Caisey et al.

[11] Patent Number: 5,587,170
[45] Date of Patent: Dec. 24, 1996

[54] COLLOIDAL SUSPENSION BASED ON INORGANIC FILLERS AS A COSMETIC COMPOSITION

[75] Inventors: Laurence Caisey, Vitry-sur-Seine; Jean M. Sturla, Saint-Cloud, both of France

[73] Assignee: L'Oreal, Paris, France

[21] Appl. No.: 430,741

[22] Filed: Apr. 28, 1995

[30] Foreign Application Priority Data

Apr. 28, 1994 [FR] France .................................. 94 05181

[51] Int. Cl.$^6$ ................................ A61K 7/00; A61K 7/02
[52] U.S. Cl. ........................ 424/401; 424/70.1; 424/61; 424/47
[58] Field of Search ................................ 424/401, 61, 47, 424/70.1, 70.4, 78.03; 514/844, 846, 861–865, 887, 880, 951, 947

[56] References Cited

U.S. PATENT DOCUMENTS 4,255,416  3/1981  Gillespie .................................. 424/80
5,049,309  9/1991  Sakamoto et al. ....................... 252/313

FOREIGN PATENT DOCUMENTS 0261560   9/1987   European Pat. Off. ..
244859   11/1987   European Pat. Off. ..
261560   3/1988   European Pat. Off. ..
1342091  12/1973   United Kingdom .

OTHER PUBLICATIONS

Derwent Publications Ltd., London, GB; AN 7756501 & JP-A-52 076 439 (Hinoki Shinyaku).

Primary Examiner—Thurman K. Page
Assistant Examiner—Sharon Howard
Attorney, Agent, or Firm—Jacobson, Price, Holman & Stern, PLLC

[57] ABSTRACT

Use of a colloidal suspension based on inorganic fillers, which can be prepared by the sol-gel process, as a cosmetic composition for treating the skin, hair and/or nails for the purpose of forming, after evaporation of the liquid medium of the suspension, an inorganic film on the skin, hair and/or nails.

12 Claims, No Drawings

COLLOIDAL SUSPENSION BASED ON INORGANIC FILLERS AS A COSMETIC COMPOSITION

The subject of the present invention is the use of colloidal suspensions based on inorganic fillers in the cosmetic treatment of the skin, hair or nails for the purpose of forming, after evaporation of the solvent medium, an inorganic film on these materials.

Colloidal suspensions based on inorganic fillers are know in themselves and have already been used in the state of the art, in particular for conferring, especially on substrates such as plastic or glassy materials, anti-reflecting properties (WO 93/04386 or FR-A-2 693 558) or alternatively for producing interferential dielectric mirrors (WO 93/08490).

Titanium dioxide sols have already been used as starting materials in the production of absorbing compositions intended to protect the skin against UV radiation.

The Applicant company has discovered, which forms the subject of the invention, that the use of colloidal suspensions based on inorganic fillers made it possible to obtain, after evaporation of the solvent, an inorganic film. This film makes it possible, in particular, to modify the reflective properties of the skin, hair or nails. Thus skin treated with an appropriate colloidal suspension can be made more matt, which has the consequence of visually disguising wrinkles. Hair treated with such a composition can exhibit improved sheen. Moreover, these suspensions confer good cosmetic properties on the skin, hair and/or nails.

The colloidal suspensions which can be used in accordance with the invention are in particular prepared by the sol-gel process, which is known in itself.

The subject of the invention is thus the use of colloidal suspensions based on inorganic fillers as a cosmetic composition for the purpose of forming, after evaporation, an inorganic film on the skin, hair or nails.

Another subject of the invention comprises the compositions employed in the context of this use.

Another subject of the invention is the use of these compositions for the purpose of modifying the reflective properties of the hair, skin or nails.

Other subjects of the invention will become apparent on reading the description and examples which follow.

The invention more particularly relates to the use of a colloidal suspension based on inorganic fillers, which can be prepared by the process known as the sol-gel process, for the purpose of forming on the skin, hair and/or nails, after evaporation of the liquid medium of the suspension, an inorganic film.

The suspension used in accordance with the invention contains, in a medium consisting of water, a water/alcohol mixture or an alcohol, at least one metal salt or oxide, in the form of particles having a refractive index of between 1.3 and 1.6 or greater than or equal to approximately 1.9 and preferably between 1.9 and 3.

By virtue of the composition in accordance with the invention, it is possible to modify the reflective properties of the skin, hair and/or nails by increasing the lustre sheen/gloss or by conferring a greater degree of mattness on the hair, skin or nails.

The Applicant company has observed that it was possible to increase the sheen of the hair by using a colloidal suspension containing a metal salt or oxide having a refractive index greater than 1.9, preferably greater than 2.1 and in particular between 1.9 and 2.9.

The Applicant company has also observed that this shiny appearance persists even after styling and the film deposited on the hair leaves the hair feeling natural, the treated hair does not stick together and moreover has entirely acceptable cosmetic properties.

The mattness properties are more particularly obtained and advantageous in the treatment of the skin. Thus the Applicant company has observed that the use of collodial suspensions containing metal salts or oxides having a refractive index of between 1.3 and 1.6 and preferably between 1.35 and 1.50 conferred on the skin a mattness without whitening, the skin is less lustrous and exhibits fewer shiny areas, which has the advantage of disguising wrinkles. These effects remained, even after rinsing.

The metal oxides which can more particularly be used in accordance with the invention are chosen from $TiO_2$, $Al_2O_3$, $Ta_2O_5$, $Nb_2O_5$, $ThO_2$, $ZrO_2$ or $HfO_2$ and their hydrates, such as $Ta_2O_5.2.6H_2O$, $Nb_2O_5.2.3H_2O$ or $Al_2O_3.H_2O$. These metal oxides make it possible in particular to contribute lustre to the skin, sheen to the hair and gloss to the nails.

Other metal oxides or salts which can be used comprise $SiO_2$, $MgF_2$ or $CaF_2$, which more particularly have the advantage of conferring a matt nature on the skin. Indeed, a visual toning down of the reflection and an effect of masking wrinkles and surface blemishes, without whitening of the skin, are observed.

The film deposited on the hair, skin and/or nails is porous and confers on these substrates a refractive index of between 1.15 and 1.35, which has the effect of giving a greater degree of mattness, or between 1.65 and 2.9, which has the effect of improving the sheen, lustre or gloss of the materials treated. These indices can be modified by varying the porosity of the film deposited.

This film is composed essentially of metal oxides or salts as defined above.

These inorganic fillers are more particularly used in the form of particles having a size of between 1 nm and 300 nm and more preferentially between 5 and 100 nm.

These particles can have a spherical or parallelepipedal or other shape.

The more particularly preferred inorganic fillers, in accordance with the invention, are titanium dioxide ($TiO_2$), which confers a sheen effect on hair, and $SiO_2$, which gives a matting effect, in particular to the skin.

The colloidal suspensions generally have a viscosity of between 1 and 5 mPa.s.

The compositions in accordance with the invention are known per se and can be prepared by processes which are well known in the state of the art. These compositions are more particularly prepared from corresponding metal salts or alkoxides dissolved in a solvent, such as an alcohol. A hydrolysis reaction is then carried out in order to form an amorphous precipitate. Dispersion is then carried out with an acid or a base, depending on the desired pH, which leads to the peptization of the precipitate and to crystallization. In this way, a crystalline oxide in a solvent is formed.

Such colloidal suspensions can be prepared according to processes which are known per se, as described in J. Colloid Interface Sci., 26, p. 62–69, 1968 for $SiO_2$, Appli. Opt., 26, 4688, 1987 for $TiO_2$, Inorg. Chem., 3, 146, 1964 for $ZrO_2$ and $HfO_2$, U.S. Pat. No. 3,256,204, 1966 for $ThO_2$, Am. Cer. Soc. Bull., 54, 289, 1975 for AtOOH, MRS, Better Ceramics Through Chemistry, 1991 for $Ta_2O_5$ and $Nb_2O_5$ and Appl. Opt., 27,3356, 1988 for $CaF_2$ and $MgF_2$.

These suspensions are prepared by using ionic precursors most often chosen from chlorides, oxychlorides, perchlorates, nitrates, oxynitrates or alternatively acetates or molecular precursors, preferably chosen from alkoxides, of molar formula $M(OR)_n$ (M representing a metal, OR an alkoxy radical containing 1 to 6 carbon atoms and n representing the valency of the metal). In the methods described above, the precursor is hydrolysed or fluorinated, then polymerized until a finished product is obtained, which is insoluble in the chosen solvent, nucleated and known as colloidal suspension. In the case of alkoxides, the hydrolysis must be strictly controlled, given the very hydrophilic nature of these organometallic derivatives.

Another process for the preparation of such products is described in J. Livage et al., "Sol-gel Synthesis of Metal Oxide Clusters and Colloids" (Mat. Res. Soc. Synt. Proc., Volume 272, pages 3 to 14).

The colloidal suspensions which can be used in accordance with the invention generally have a concentration of inorganic fillers in suspension of between 0.001% and 25%, and preferably between 0.05% and 10%, by weight with respect to the total weight of the colloidal suspension.

The medium which can be used can consist of water or a water/alcohol mixture or an alcohol. The alcohols are chosen more particularly from lower alcohols having between 1 and 4 carbon atoms, such as ethanol or isopropanol, or polyols, such as propylene glycol, glycerol and sorbitol.

The pH of these compositions is generally between 5 and 10 and preferably between 6 and 9 and can be adjusted by cosmetically acceptable basifying or acidifying agents which are known per se.

The compositions in accordance with the invention can also contain various, preferably non-ionic, additives such as more particularly non-ionic surface-active agents like the alkylphenoxypolyethoxyethanols, such as octylphenoxypolyethoxyethanol, the number of ethoxy groups being between 2 and 10.

The compositions can also contain silicones, non-ionic polymers, such as polyvinyl alcohol, polyvinylpyrrolidone or polyvinylbutyral, or glycerols.

It is also possible to add to these compositions dyes having the aim of colouring the composition or the hair or the skin, anti-free-radical agents, moisturizing agents, sunscreening agents for protecting the skin against the effects of UV radiation and any other additive which does not have a destabilizing effect on the colloidal suspension or on the film which this colloidal suspension forms on the hair, skin and/or nails.

These compositions can contain, as dyes, direct dyes or pigments, such as the pigments derived from melanin, in proportions of between 0.1 and 10% with respect to the inorganic fillers used in accordance with the invention. It is more particularly possible to use the melanin pigments derived in particular from the oxidation of 5,6-dihydroxyindole or of its derivatives, as well as melanin pigments of natural origin or alternatively coloured iron oxide.

The compositions which can be used in accordance with the invention can be applied in the aerosol, gel or lotion form. The application of these products can optionally be followed by a rinsing.

The product used in accordance with the invention is sprayed onto the hair. After drying, it is observed that a film has formed which, when the inorganic filler is composed of an agent having a refractive index greater than 1.9, gives a greater sheen while conferring advantageous cosmetic properties, such as softness to the touch and disentangling, on the hair.

To treat the skin, the colloidal suspension can be sprayed from a pump-action spray. After drying and optional rinsing, it is observed, when the inorganic filler used has a refractive index of less than 1.6, that there is less reflection and a disguising of wrinkles.

The following examples are intended to illustrate the invention without having in any way a limiting nature.

EXAMPLE 1

An aqueous colloidal suspension, containing 4.5% by weight of titanium dioxide ($TiO_2$), is applied to the hair by spraying. The viscosity of this suspension is 1.1S mPa.s and its pH is 10. The $TiO_2$ particles have a mean particle size of approximately 22 nm.

After spraying, the hair is left to dry. A fine film is deposited. The hair is shaped and it is observed that the hair has a shiny appearance which remains after styling. Moreover, the hair has a natural feel which is not sticky and has good cosmetic properties.

EXAMPLE 2

A colloidal suspension, comprising 3.5% of $SiO_2$ with a particle size of 26 nm in ethanol, is sprayed onto the skin. This sol has a pH of 7.5. After drying, it is observed that the skin has a much more matt appearance, which has the consequence of disguising wrinkles. The skin retains its colour and does not whiten.

EXAMPLE 3

The following composition is prepared:

| | |
|---|---|
| $TiO_2$ (mean particle size 29 nm) | 3% by weight, |
| Water qs | 100 g |
| pH = 9 | |

This composition is applied by spraying onto the nails. It is observed that there is an increase in the gloss of the nails after drying. This effect is maintained even after rinsing with water.

EXAMPLE 4

The following composition is prepared:

| | |
|---|---|
| $TiO_2$ | 3% by weight |
| Polyvinylpyrrolidone | 0.3% |
| Water | q.s. for 100 g |

This composition is applied to the hair. The hair, once dried, is shiny and this sheen effect is maintained after styling and shaping.

We claim:

1. Process for cosmetic treatment of the skin, hair and/or nails, comprising applying a colloidal suspension containing, in a cosmetic medium consisting of water, a water/alcohol mixture or an alcohol, metal salts or oxides in the form of particles having a refractive index greater than or equal to approximately 1.9 or between 1.3 and 1.6 inclusive on the skin, hair and/or nails in order to form, after evaporation of the cosmetic medium of the suspension, a film of the metal salts or oxides which modifies the reflective properties of the skin, hair and/or nails.

2. Process according to claim 1, wherein the metal oxides are $TiO_2$, $Al_2O_3$, $Nb_2O_5$, $ZrO_2$, or $NfO_2$, or their hydrates, which confer properties of lustre/sheen/gloss on the skin, hair and/or nails.

3. Process according to claim 1, wherein the metal salts or oxides are $SiO_2$, $MgF_2$ or $CaF_2$ which confer a matt appearance on the skin and/or hair.

4. Process according to claim 1, wherein the metal oxide is $TiO_2$ which increases the sheen of the hair.

5. Process according to claim 1, wherein the metal oxide is $SiO_2$ which visually disguises wrinkles on the skin.

6. Process according to claim 1, wherein the film formed on the skin has a refractive index of between 1.15 and 1.35 and between 1.65 and 2.9.

7. Process according to claim 1, wherein the colloidal suspension contains between 0.001% and 25% by weight of the metal salts or oxides with respect to the total weight of the suspension.

8. Process according to claim 1, wherein the colloidal suspension contains between 0.05% and 10% by weight of the metal salts or oxides with respect to the total weight of the suspension.

9. Process according to claim 1, wherein the particles of metal salts or oxides have a mean particle size of between 1 and 300 nm.

10. Process according to claim 1, wherein the particles of metal salts or oxides have a mean particle size of between 5 and 100 nm.

11. Process according to claim 1, wherein the colloidal suspension is sprayed onto the hair, skin and/or nails and is left to dry.

12. Process according to claim 11, wherein after drying of the applied colloidal suspension the skin and/or hair is rinsed.

\* \* \* \* \*